US007799059B2

(12) United States Patent
Kramer et al.

(10) Patent No.: US 7,799,059 B2
(45) Date of Patent: Sep. 21, 2010

(54) OFFSET ORTHOPEDIC FIXATION DEVICE WITH LOCKING MECHANISM

(75) Inventors: Ulrich Kramer, Tuttlingen (DE); Joerg Schumacher, Tuttlingen (DE); Michael Potulski, Ohlstadt (DE); Rudolf Beisse, Seehausen (DE); Jeffrey Alan Kozak, Houston, TX (US)

(73) Assignee: Aesculap AG, Tuttlingen (DE)

( * ) Notice: Subject to any disclaimer, the term of this patent is extended or adjusted under 35 U.S.C. 154(b) by 954 days.

(21) Appl. No.: 11/068,729

(22) Filed: Feb. 28, 2005

(65) Prior Publication Data
US 2006/0004359 A1    Jan. 5, 2006

Related U.S. Application Data

(63) Continuation of application No. PCT/EP2002/009879, filed on Sep. 4, 2002.

(51) Int. Cl.
*A61B 17/70* (2006.01)
(52) U.S. Cl. ........................ 606/256; 606/278
(58) Field of Classification Search ......... 606/267–272, 606/289, 293, 276, 278
See application file for complete search history.

(56) References Cited

U.S. PATENT DOCUMENTS

| 5,002,542 | A | * | 3/1991 | Frigg ........................ 606/264 |
| 5,129,900 | A | * | 7/1992 | Asher et al. ................ 606/264 |
| 5,176,679 | A | * | 1/1993 | Lin ............................ 606/272 |
| 5,474,551 | A | | 12/1995 | Finn et al. |
| 5,476,463 | A | | 12/1995 | Boachie-Adjei et al. |
| 5,545,228 | A | | 8/1996 | Kambin |
| 5,611,800 | A | * | 3/1997 | Davis et al. ................ 606/250 |
| 5,645,544 | A | * | 7/1997 | Tai et al. .................... 606/259 |
| 5,713,900 | A | * | 2/1998 | Benzel et al. .............. 606/250 |
| 5,741,255 | A | * | 4/1998 | Krag et al. ................. 606/264 |
| 5,876,402 | A | | 3/1999 | Errico et al. |
| 5,921,985 | A | * | 7/1999 | Ross et al. ................... 606/59 |
| 6,520,962 | B1 | * | 2/2003 | Taylor et al. ............... 606/278 |
| 6,569,164 | B1 | * | 5/2003 | Assaker et al. ............. 606/250 |
| 6,602,253 | B2 | * | 8/2003 | Richelsoph et al. ........ 606/252 |
| 6,958,066 | B2 | * | 10/2005 | Richelsoph et al. ........ 606/252 |
| 7,141,051 | B2 | * | 11/2006 | Janowski et al. ........... 606/272 |
| 2002/0111625 | A1 | * | 8/2002 | Richelsoph et al. .......... 606/61 |
| 2002/0120272 | A1 | * | 8/2002 | Yuan et al. .................... 606/61 |
| 2002/0120273 | A1 | * | 8/2002 | Needham et al. ............. 606/61 |
| 2005/0187551 | A1 | * | 8/2005 | Orbay et al. .................. 606/69 |
| 2006/0149253 | A1 | * | 7/2006 | Doubler et al. ............... 606/69 |
| 2006/0149255 | A1 | * | 7/2006 | Doubler et al. ............... 606/69 |

FOREIGN PATENT DOCUMENTS

WO    WO 99/55246 A1 * 11/1999

* cited by examiner

*Primary Examiner*—Thomas C Barrett
*Assistant Examiner*—Michael J Araj
(74) *Attorney, Agent, or Firm*—Lipsitz & McAllister, LLC

(57) ABSTRACT

The invention relates to an orthopedic fixation device with an at least partly shaft-like fixation member, a shaft-like mounting body, and a transverse support securing the fixation member and the mounting body in a position in which they are laterally offset from one another. In order to adjust the transverse support without having to change the position of the fixation member, the fixation member can be rotated about its longitudinal axis in the transverse support and can be secured in a defined angular position.

19 Claims, 5 Drawing Sheets

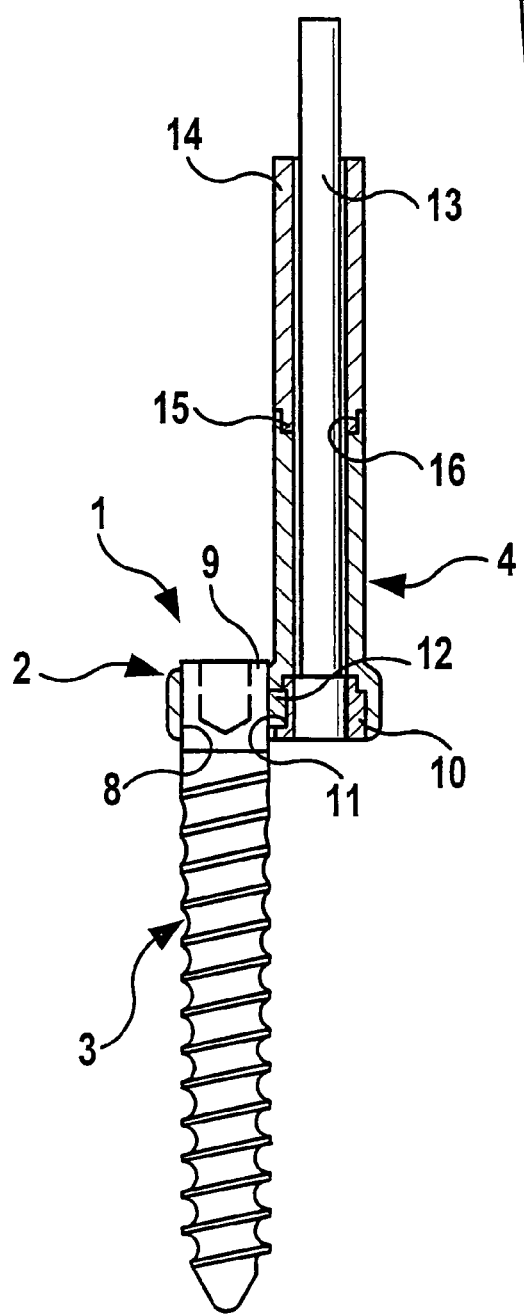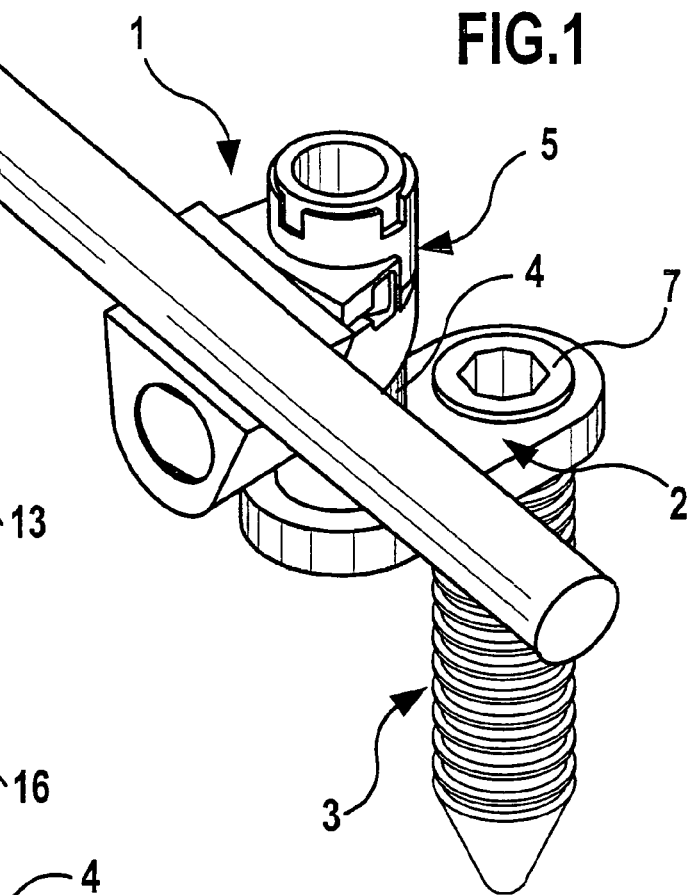

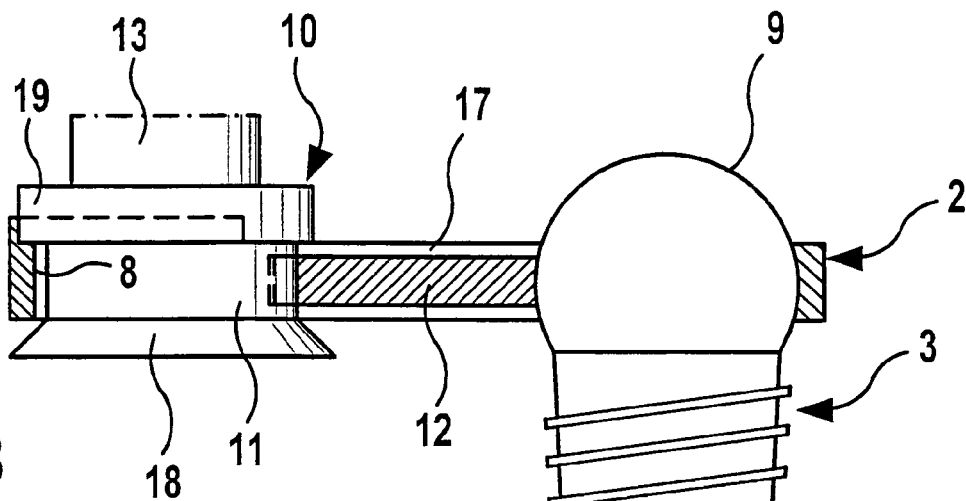
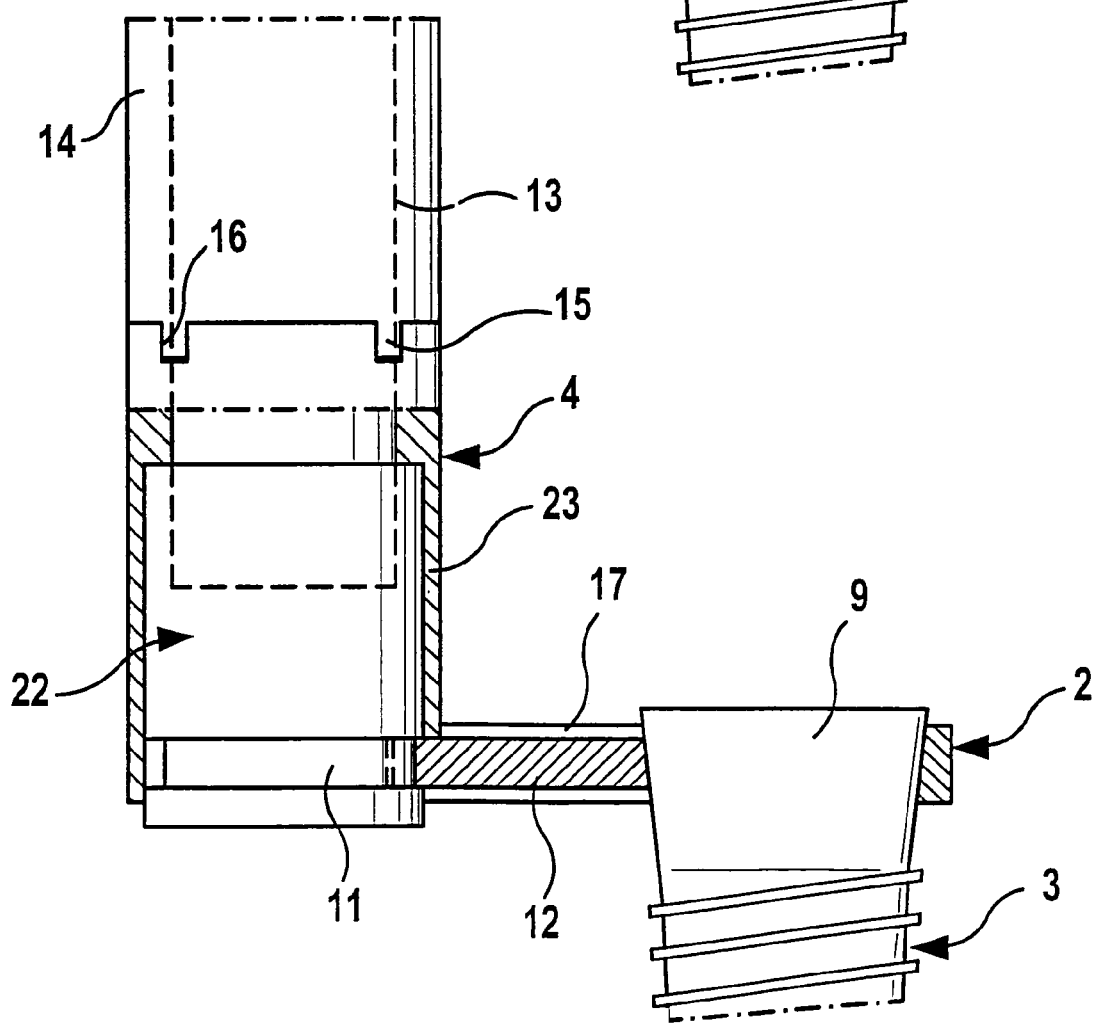

OFFSET ORTHOPEDIC FIXATION DEVICE WITH LOCKING MECHANISM

This application is a continuation of international application No. PCT/EP2002/009879 filed on Sep. 4, 2002, which is incorporated herein by reference in its entirety and for all purposes.

BACKGROUND

The invention relates to an orthopedic fixation device with an at least partly shaft-like fixation member, with a shaft-like mounting body, and with a transverse support securing the fixation member and the mounting body in a position in which they are laterally offset from one another.

A fixation device of this kind is known, for example, from U.S. Pat. No. 5,545,228 in which a fixation member in the form of a bone screw carries a transverse support which is connected fixedly to it and at whose other end a mounting body in the form of an externally threaded pin is disposed. With this arrangement, it is possible for the mounting body to be disposed in a position laterally offset from the fixation member. In this way the operating surgeon, for example when using an orthopedic fixation device, is given greater freedom in positioning the externally threaded pin with respect to the bone screw, and all that needs to be done is to screw the bone screw into the bone in a different angular position. However, in order to adjust the position of the transverse support, it is necessary also to turn the bone screw in the bone, and this can lead to undesired loosening of a screw once in place.

It is an object of the invention to further develop an orthopedic fixation device of the generic type so that the position of the mounting body relative to the fixation member can also be adjusted without having to change the fixation setting of the fixation member.

SUMMARY OF THE INVENTION

In the case of an orthopedic fixation device of the type described at the outset, this object is achieved, according to the invention, by the fact that the fixation member can be rotated about its longitudinal axis in the transverse support and can be secured in a defined angular position.

Thus, the transverse support in the released position can be rotated relative to the fixation member, while the latter remains in its adopted position. The transverse support can be adjusted to a different angular position relative to the fixation member. In the released position, the fixation member can additionally be displaced in the longitudinal direction too, so that, at the same time as the fixation member is secured in a defined angular position, it is also secured in a defined axial position.

For securing the transverse support on the fixation member, it is advantageous if the latter can be clamped in a defined angular position and/or axial position.

In a preferred embodiment of the invention, in order to permit clamping in the transverse support, a clamp piece can be moved against the fixation member.

In order to move the clamp piece in the transverse support, it is possible in particular for a tensioning member to be mounted so that it engages against the clamp piece and is rotatable about a rotation axis. This affords a very compact configuration with which the transverse support can be released or secured relative to the fixation member. It is advantageous here if the angle of rotation of the tensioning member is limited in one direction or in both directions, for example by a limit stop. In this way, it is possible in particular to avoid a situation where the clamp piece is tensioned too strongly against the fixation member, which could result in the whole device being damaged. The defined rotatability between two end points also makes handling of the device easier for the operating surgeon.

The tensioning member may also take the form of a stressing member which places a stress on the clamp piece or a loading member which exerts a compressive load on the clamp piece.

The rotation axis of the tensioning member is preferably perpendicular to the plane of the transverse support, and it is advantageous if the rotation axis of the tensioning member extends parallel to the longitudinal axis of the fixation member.

A particularly advantageous construction is obtained if the transverse support has an oblong hole in which the fixation member, the clamp piece and the tensioning member are accommodated. This affords an especially space-saving and compact configuration which, if appropriate, allows the fixation member and the mounting body to be disposed very closely alongside one another.

An especially space-saving configuration is obtained if, according to a preferred embodiment, the rotation axis of the tensioning member and the longitudinal axis of the mounting body coincide. The tensioning member is then disposed concentrically with respect to the mounting body, and no additional space is then required for the provision and the rotation of the tensioning member.

For example, the mounting body can be a sleeve which is connected fixedly to the transverse support and through which a tool can be inserted for rotating the tensioning member.

It is advantageous here if the mounting body has seats for a stabilizing tool with which the mounting body, upon tensioning of the tensioning member, can be held securely so that no undesired torques are applied to the transverse support during tensioning of the tensioning member.

In another embodiment, the tensioning member is a ring which is rotatable in the transverse support and which is disposed at the transverse support end of the mounting body.

In another embodiment, the tensioning member can also be disposed on a core which is mounted rotatably in the mounting body and which, at least along part of its length, extends inside the mounting body.

In a modified embodiment, the mounting body can rotate about its longitudinal axis in the transverse support and itself carries the tensioning member.

It is advantageous if the tensioning member is secured in the axial direction in the transverse support.

In a particularly preferred embodiment, the tensioning member has a cam (a loading member) which is disposed eccentrically with respect to its rotation axis and engages against the clamp piece.

In another preferred embodiment, the tensioning member has an inclined path curve engaging against the clamp piece.

Provision can be made to ensure that, when the axially immovable tensioning member is rotated parallel to the rotation axis, the path curve moves the clamp piece against the fixation member and thereby clamps the latter.

It is advantageous if the fixation member has a widening shaft, against which the clamp piece engages, and is mounted so as to be axially immovable and freely rotatable in the transverse support. The axial movement of the clamp piece thus secures the fixation member.

It is also possible to superpose the action of a cam and the action of a tensioning member acting in the axial direction.

In a modified embodiment, it is also possible for the fixation member to be connected pivotably to the transverse support via a spherical connection, and for the clamp piece to be moved in the direction of a spherical bearing surface of the fixation member at the time of fixing.

The fixation member can be any desired shaft-like, hook-like or pin-like component of a fixation device, and the fixation member is particularly preferably formed as a bone screw or as a hook.

BRIEF DESCRIPTION OF THE DRAWINGS

The present invention will hereinafter be described in conjunction with the appended drawing figures, wherein like reference numerals denote like elements, and:

FIG. 1 shows a perspective view of an orthopedic fixation device for securing a rod-shaped connection member;

FIG. 2 shows a longitudinal section through a preferred illustrative embodiment of an orthopedic fixation device;

FIG. 7 shows a view similar to FIG. 5, in this case of a fixation member with a spherical head;

FIG. 8 shows a view similar to FIG. 5 in another preferred illustrative embodiment with a cam in the form of a rotatable core and with a mounting body surrounding the latter and fixedly connected to the transverse support;

DETAILED DESCRIPTION

Figure 3:
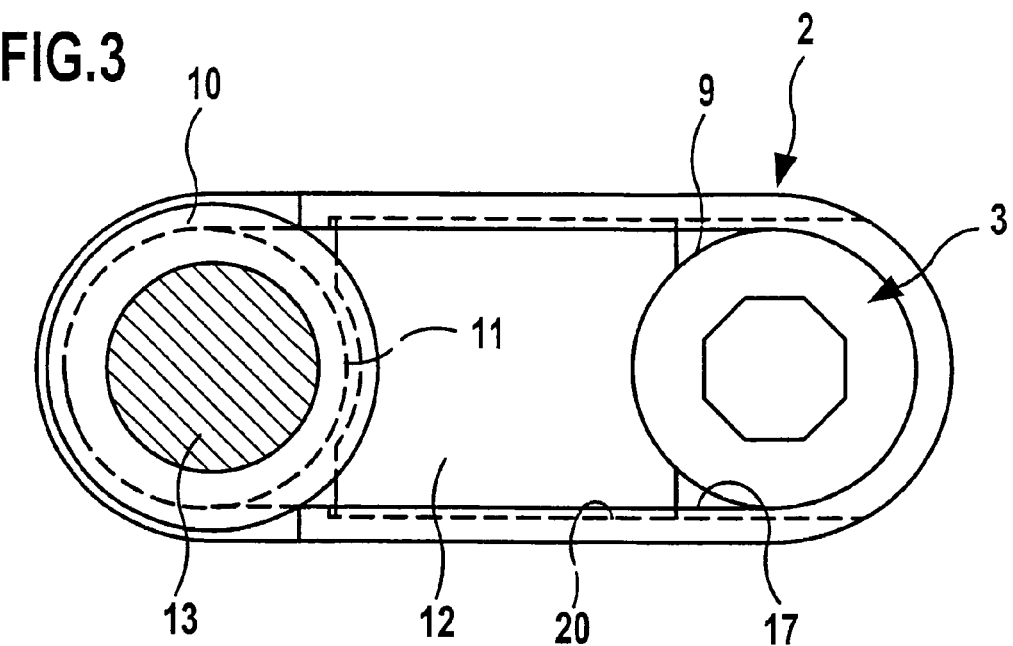
FIG. 3 shows a plan view of a preferred illustrative embodiment of a transverse support with a clamp piece which can be moved by a cam and which is shown here in the released position.

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The fixation device 1 shown in FIG. 1 comprises a bone screw 3 with a plate-shaped transverse support 2 which can be secured at the upper end of the bone screw 3 and which in turn carries a sleeve-like, cylindrical mounting body 4. The bone screw 3 and the mounting body 4 are disposed parallel to one another and are laterally offset from one another by the transverse support 2.

A retaining device 5, shown in FIG. 1 but not explained in any more detail, can be fitted onto the mounting body and secures, for example, a rod-shaped connection element 6 on the mounting body 4, which connection element 6 connects the illustrated fixation device 1 to a similarly constructed fixation device, both fixation devices being secured via their bone screws 3 on different bones or bone fragments which are in this way positioned and fixed relative to one another.

The transverse support 2 is mounted on the bone screw 3 so that it can rotate about the longitudinal axis of the bone screw 3, and it can be secured in different angular positions relative to the bone screw 3 by suitable means. This can be done, for example, by a clamping ring 7 secured on the bone screw 3 being pressed in the longitudinal direction of the bone screw 3 against the transverse support 2, and this itself can be screwed into the bone screw 3 for example. This is shown only very schematically in the illustration in FIG. 1, but it is nonetheless quite clear from this illustration that, by rotating the transverse support 2 relative to the bone screw 3, the whole fixation device 1 can be adjusted to a considerable extent in terms of its position relative to the bone screw 3 and thus in terms of its position relative to the bone part in which the bone screw 3 is screwed, and it is possible to do this without having to change the position of the bone screw 3 relative to the bone part.

In the illustrative embodiment in FIG. 2, the transverse support has an insertion opening 8 through which a cylindrical shaft 9 of the bone screw 3 is passed. As in the illustrative embodiment in FIG. 1, the mounting body 4 is formed as a sleeve and is connected fixedly to the transverse support 2. Alongside the insertion opening 8, and concentric with respect to the mounting body 4, a ring 10 is mounted rotatably in the transverse support 2, its outer surface being formed eccentrically with respect to its rotation axis, forming cam 11. Between the outer surface of cam 11 and the insertion opening 8, a clamp piece 12 is mounted displaceably in the inside of the transverse support 2 and, when the ring 10 is rotated, this clamp piece 12 can be forced by the eccentricity of the cam 11 against the shaft 9 of the bone screw 3 inserted into the insertion opening 8, so that this shaft 9 is thereby clamped in the insertion opening 8.

In order to rotate the ring 10, a rotary tool 13 can be introduced into the sleeve-shaped mounting body 4 and engages in a rotationally fixed manner in the ring 10. In addition, a stabilizing tool 14 is provided which is formed as a sleeve, surrounds the rotary tool 13 and is pushed from above onto the likewise sleeve-shaped mounting body 4. With the latter, it forms a rotationally fixed connection through the engagement of projections 15 into recesses 16, this connection making it possible, upon rotation of the rotary tool 13, to hold the mounting body 4 by means of the stabilizing tool 14 so that no undesired torques are transmitted to the transverse support 2.

The configuration shown in FIG. 2 is of particularly compact construction, because the longitudinal axis of the mounting body 4 coincides with the rotation axis of the ring 10, and it will be seen from the illustration in FIG. 2 that the transverse support can be made so short that bone screw 3 and mounting body 4 can lie directly alongside one another.

Figure 4:
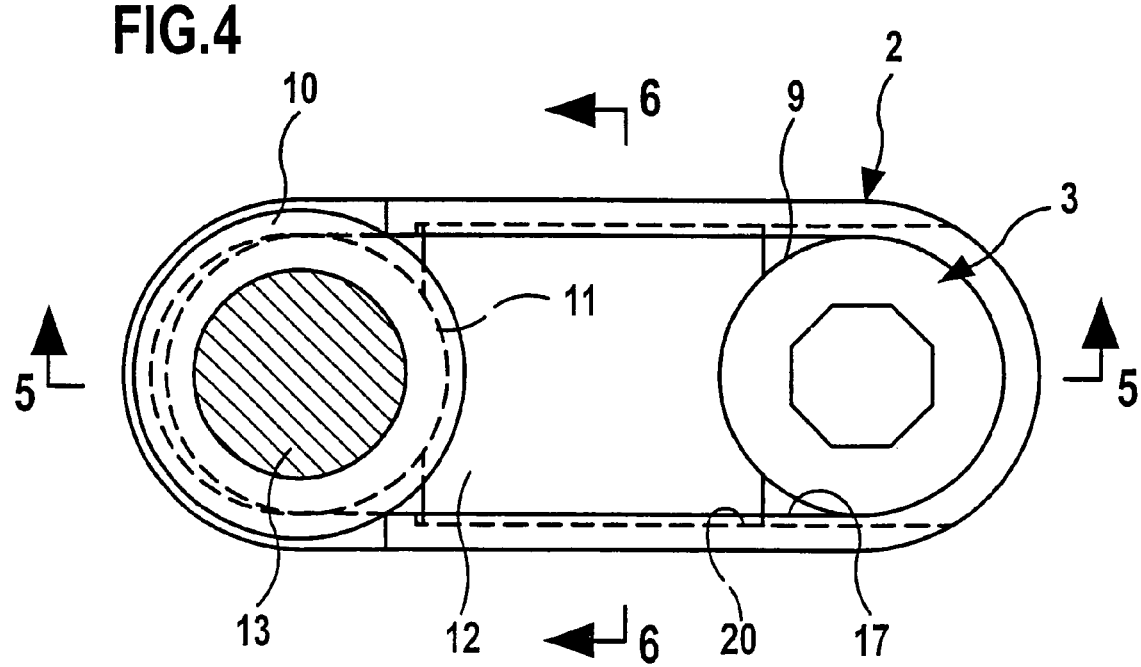
FIG. 4 shows a view similar to FIG. 3, with the clamp piece in the tensioned position.
Figure 5:
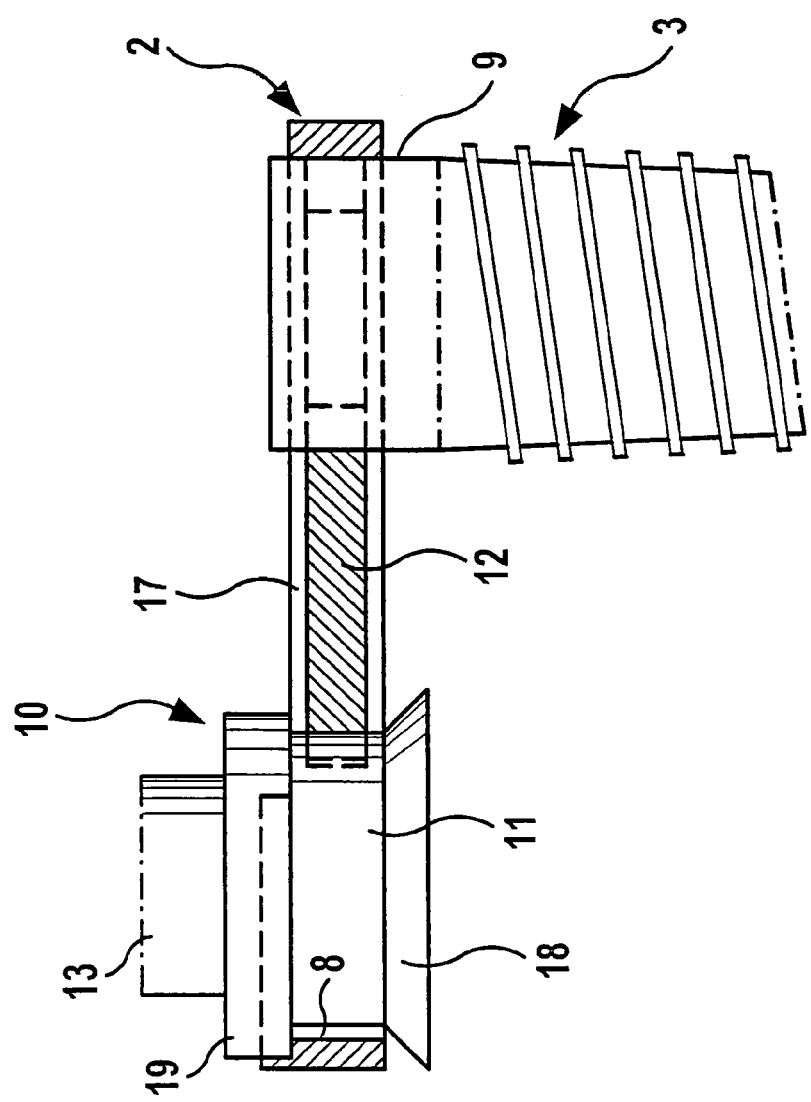
FIG. 5 shows a sectional view along line 5-5 in FIG. 4.

In other embodiments, the transverse support 2 can also be made longer, in which case the clamp piece 12 is also made correspondingly longer, as is shown in the example in FIGS. 3 to 5. This transverse support 2 is formed as a flat, strip-shaped plate and has an oblong hole 17 extending along a large part of its length. The shaft 9 of the bone screw 3 is inserted through this oblong hole 17, and on the other side the ring 10 is mounted rotatably in the oblong hole 17 and is secured in the axial direction by a lower annular flange 18 and an upper annular flange 19. Between the shaft 9 and the ring 10 there is once again a clamp piece 12 which is guided displaceably in the oblong hole and which at one end engages against the cam 11 and at the other end engages against the shaft 9.

In this illustrative embodiment, the sleeve-shaped mounting body 4 is not shown, but it is possible to provide the latter disposed on the transverse support 2 and surrounding the ring 10.

Figure 6:
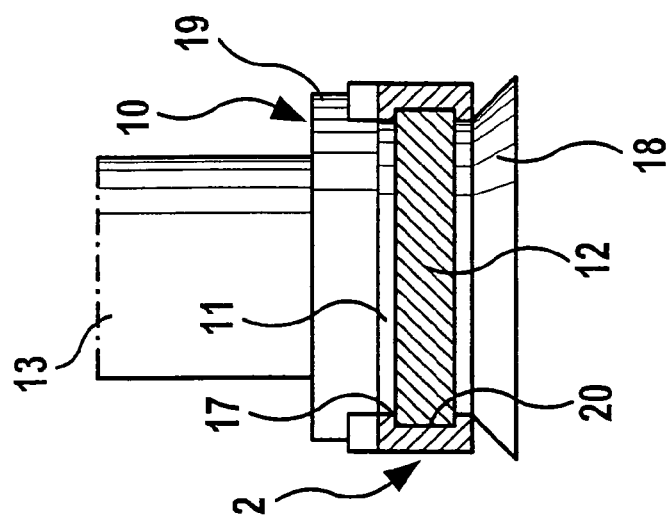
FIG. 6 shows a sectional view along line 6-6 in FIG. 4.

It will be seen clearly from the illustration in FIG. 6 that the clamp piece 12 is guided in the oblong hole 17 in lateral grooves 20 of the transverse support 2, in the longitudinal direction of the latter, so that the clamp piece 12 is held captive in the transverse support 2.

In the illustrative embodiment in FIG. 7, a bone screw 3 is shown whose shaft 9 does not have a circular cylindrical form, but is instead spherical. This gives the transverse support 2 an additional degree of freedom, and between transverse support 2 and bone screw 3 a spherical articulation is formed which, however, can be secured in the same way by moving the clamp piece 12 against the shaft 9.

In the illustrative embodiment in FIG. 8, which is of a similar construction to that in FIGS. 3 to 7 and in which identical parts carry the same reference numbers, a bone screw 3 is shown with a shaft 9 widening conically toward the top. These shaft shapes of the bone screws 3 are of course interchangeable between the different illustrative embodiments.

The illustrative embodiment in FIG. 8 also shows that the cam 11 is not disposed on a ring here, but instead on a rotatable core 22 which projects upward from the transverse support 2 and into a sleeve 23 which is fixedly connected, for example welded, to the transverse support 2 and which in this case forms the mounting body 4. As in the illustrative embodiment in FIG. 2, a rotary tool 13 can be pushed from above into the sleeve 23 and can there establish a rotationally fixed connection with the core 22 by means of a suitable positive fit.

The illustrative embodiment in FIG. 8 also shows a stabilizing tool 14 which is sleeve-shaped, like the sleeve 23, and can be placed from above onto the sleeve 23 in such a way that projections 15 on the stabilizing tool 14 engage in corresponding recesses 16 on the sleeve 23 and thus establish a rotationally fixed connection. The stabilizing tool 14 allows the sleeve 23 to be held secure as the core 22 is being rotated, so that no undesired torques are transmitted to the transverse support 2.

Figure 9:
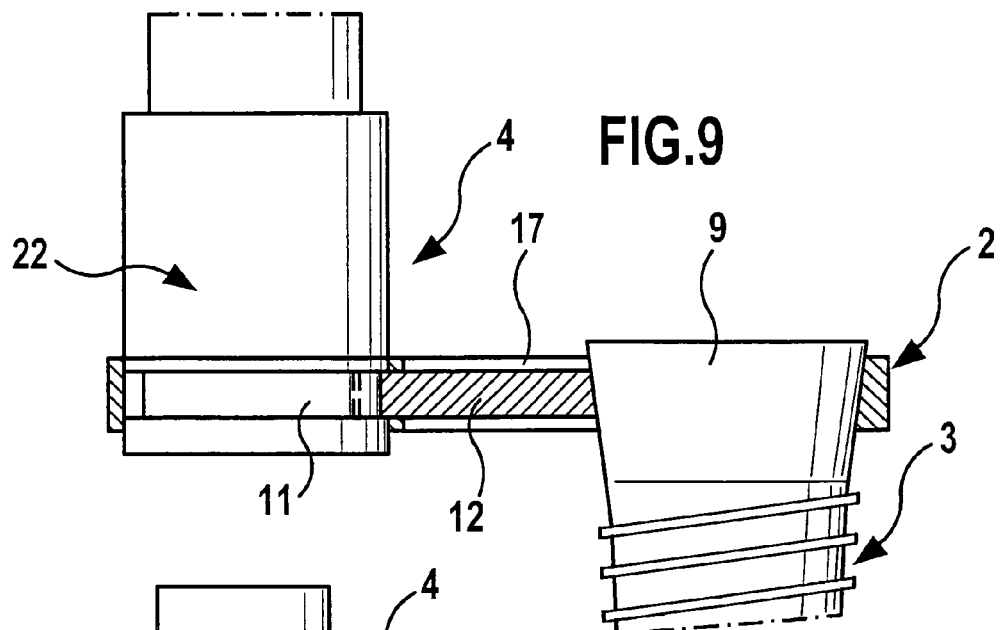
FIG. 9 shows a further preferred embodiment with a mounting body which at the same time carries the cam for tensioning of the clamp piece.

In the illustrative embodiment in FIG. 9, there is no mounting body in the form of a sleeve, and instead the core 22 itself forms the mounting body 4. In the illustrative embodiment in FIG. 9, this core 22 has a stepped formation, although it would also be possible for it to have a continuous circular cylindrical form. In this case, the core 22 itself serves for the retention of further orthopedic fixation elements.

In the illustrative embodiments in FIGS. 1 to 9, the clamp piece 12 is forced by a cam 11 against the bone screw 3, which by this means is held against rotation and, if appropriate, also against axial movement.

Figure 10:
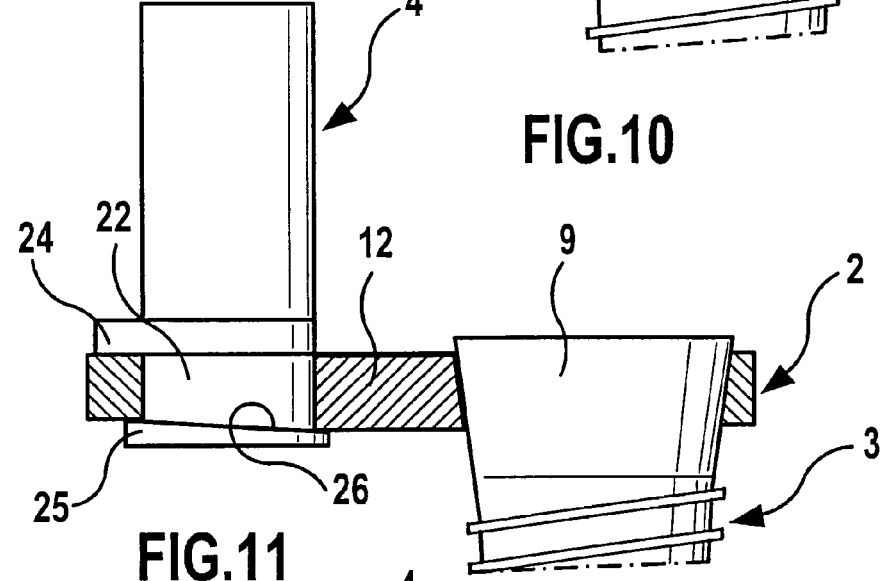
FIG. 10 shows a further preferred embodiment similar to that in FIG. 9, with a curved path for axial displacement of the clamp piece.

In the illustrative embodiment in FIG. 10, by contrast, in which corresponding parts once again carry the same reference numbers, no such cam is present. Instead, the mounting body 4 mounted rotatably in the transverse support 2 is secured axially in the transverse support 2 by two annular flanges 24, 25. The shaft 9 of the bone screw 3 widens conically toward the top, and the clamp piece 12 lying in between is adapted to this contour. The bone screw 3 is also secured in the axial direction in the transverse support 2 by means not apparent from the drawing, but it is freely rotatable in said transverse support 2.

The top face of the lower annular flange 25 engages under the clamp piece 12, said top face being inclined slightly with respect to a plane which is perpendicular to the rotation axis of the mounting body 4 formed as core 22. The top face of the lower annular flange 25 thus forms an inclined path curve 26 which, when the mounting body 4 is rotated, moves the clamp piece 12 parallel to the rotation axis. As a result of the conical configuration of the shaft 9, it thus grips the bone screw 3 and thereby secures this bone screw 3 against rotation. Whereas, in the case of the cam 11, the movement of the clamp piece is effected transverse to the rotation axis of the cam, in this configuration the clamp piece is moved parallel to the rotation axis of the mounting body 4. This configuration can be used instead of the cam in all of the embodiments described above, or both actions can be combined.

Figure 11:
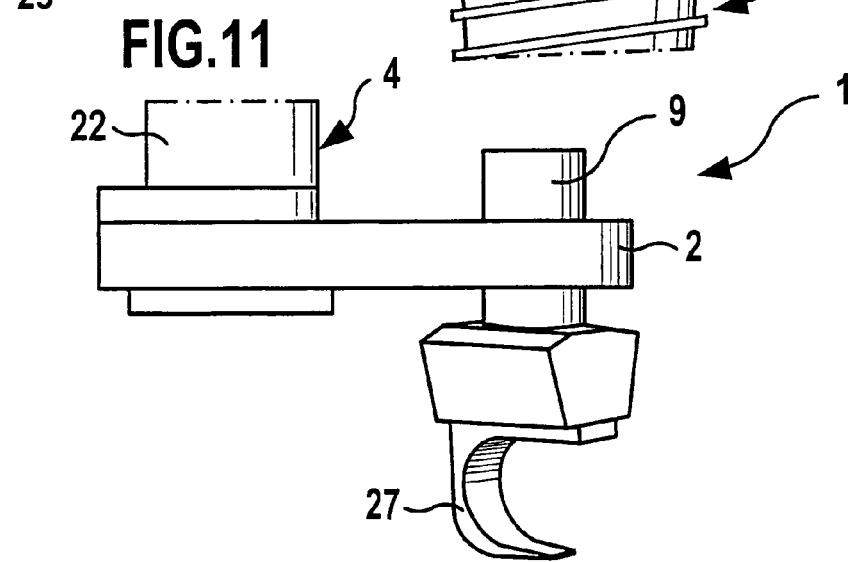
FIG. 11 shows a further preferred embodiment of an orthopedic fixation device with a fixation member in the form of a hook.

FIG. 11 shows a further modified illustrative embodiment of a fixation device 1; this can be of substantially the same construction as the above-described fixation devices, and identical parts therefore carry the same reference numbers. In contrast to the illustrative embodiments in FIGS. 1 to 10, the fixation member in this case is not formed by a bone screw, but by a hook 27 which, for example, can engage round an osseous structure in a patient's body. This hook 27 carries a shaft 9 which, in the same way as the shaft 9 of the bone screw 3 in the above-described illustrative embodiments, is freely rotatable in relation to a transverse support 2 and can be clamped both in respect of its angular position and also, if appropriate, in respect of its axial position.

What is claimed is:

1. Orthopedic fixation device, comprising:
a fixation member, said fixation member being at least partly shaft-like with a first longitudinal axis;
a shaft-like mounting body with a second longitudinal axis;
a transverse support securing the fixation member and the mounting body in a position in which the first longitudinal axis of the fixation member and the second longitudinal axis of the shaft-like mounting body are parallel to and laterally offset from one another, said transverse support being rotatable about the first longitudinal axis of said fixation member;
a clamp piece longitudinally movable within said transverse support against the fixation member and adapted for clamping of the transverse support in a defined angular position relative to the fixation member; and
a tensioning member mounted for engagement against the clamp piece, the tensioning member being rotatable about a rotation axis in order to move the clamp piece in the transverse support, the tensioning member having a cam which is disposed eccentrically with respect to the rotation axis and which engages against the clamp piece.

2. Device according to claim 1, wherein the rotation axis of the tensioning member is perpendicular to a plane of the transverse support.

3. Device according to claim 2, wherein the rotation axis of the tensioning member extends parallel to the longitudinal axis of the fixation member.

4. Device according to claim 1, wherein the transverse support has an oblong hole in which the fixation member, the clamp piece, and the tensioning member are accommodated.

5. Device according to claim 1, wherein the rotation axis of the tensioning member and second longitudinal axis of the mounting body coincide.

6. Device according to claim 5, wherein the mounting body is a sleeve which is fixedly connected to the transverse support and through which a tool can be inserted for rotating the tensioning member.

7. Device according to claim 6, wherein the mounting body has seats for a stabilizing tool.

8. Device according to claim 7, wherein the tensioning member is disposed on a ring which is rotatable in the transverse support and which is located at the transverse support end of the mounting body.

9. Device according to claim 7, wherein the tensioning member is disposed on a core which is mounted rotatably in the mounting body and which, at least along part of its length, extends inside the mounting body.

10. Device according to claim 6, wherein the tensioning member is disposed on a ring which is rotatable in the transverse support and which is located at a transverse support end of the mounting body.

11. Device according to claim 6, wherein the tensioning member is disposed on a core which is mounted rotatably in the mounting body and which, at least along part of its length, extends inside the mounting body.

12. Device according to claim 6, wherein the mounting body is rotatable about the second longitudinal axis in the transverse support and itself carries the tensioning member.

13. Device according to claim 1, wherein the tensioning member is secured in the axial direction in the transverse support.

14. Device according to claim 1, wherein the tensioning member has an inclined path curve engaging against the clamp piece.

15. Device according to claim 14, wherein, when the tensioning member is rotated parallel to the rotation axis, the path curve pushes the clamp piece against the fixation member and thereby clamps the fixation member.

16. Device according to claim 15, wherein the fixation member has a widening shaft, against which the clamp piece engages, and is mounted so as to be axially immovable and freely rotatable in the transverse support.

17. Device according to claim 1, wherein:
the fixation member is connected pivotably to the transverse support via a spherical connection, and
the clamp piece is, at the time of fixing, movable in the direction of a spherical bearing surface of the fixation member.

18. Device according to claim 1, wherein the fixation member is a bone screw.

19. Device according to claim 1, wherein the fixation member is a hook.

* * * * *